(12) United States Patent
Kawajiri et al.

(10) Patent No.: US 9,759,790 B2
(45) Date of Patent: Sep. 12, 2017

(54) MAGNETIC RESONANCE IMAGING DEVICE

(71) Applicant: TOSHIBA MEDICAL SYSTEMS CORPORATION, Otawara-shi (JP)

(72) Inventors: Sho Kawajiri, Nasushiobara (JP); Motohisa Yokoi, Nasushiobara (JP); Motohiro Miura, Yaita (JP); Masashi Hori, Nasushiobara (JP); Kazuyuki Soejima, Nasushiobara (JP); Naoki Imamura, Nasushiobara (JP); Haruki Nakamura, Nasushiobara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 718 days.

(21) Appl. No.: 14/314,465

(22) Filed: Jun. 25, 2014

(65) Prior Publication Data

US 2014/0300362 A1     Oct. 9, 2014

Related U.S. Application Data

(63) Continuation of application No. PCT/JP2013/068748, filed on Jul. 9, 2013.

(30) Foreign Application Priority Data

Jul. 9, 2012   (JP) ................................ 2012-153831

(51) Int. Cl.
*G01V 3/00*    (2006.01)
*G01R 33/385*  (2006.01)
(Continued)

(52) U.S. Cl.
CPC .......... *G01R 33/3852* (2013.01); *A61B 5/055* (2013.01); *G01R 33/5616* (2013.01)

(58) Field of Classification Search
CPC ................................................ G01R 33/3852
(Continued)

(56) References Cited

U.S. PATENT DOCUMENTS 5,311,136 A * 5/1994 Takahashi .......... G01R 33/3852
                                                        324/318
6,069,806 A * 5/2000 Lenz ................. H02M 3/33576
                                                         363/67
(Continued)

FOREIGN PATENT DOCUMENTS

JP      6-254063      9/1994
JP      10-5189       1/1998
(Continued)

OTHER PUBLICATIONS

International Search Report for PCT/JP2013/068748 mailed Aug. 6, 2013.

*Primary Examiner* — Louis Arana
(74) *Attorney, Agent, or Firm* — Nixon & Vanderhye P.C.

(57) ABSTRACT

A magnetic resonance imaging device according to an embodiment includes a gradient amplifier, a battery, a detector, and a battery controller. The gradient amplifier supplies electric power to the gradient coil. The battery is charged with electric power that is supplied from the power supply. The detector detects a high power output request on the gradient amplifier. The battery controller controls to supply electric power charged in the battery in addition to electric power supplied from the power supply to the gradient amplifier when the high power output request is detected.

10 Claims, 6 Drawing Sheets

(51) Int. Cl.
*A61B 5/055* (2006.01)
*G01R 33/561* (2006.01)

(58) Field of Classification Search
USPC .......................... 324/322, 318, 314
See application file for complete search history.

(56) References Cited

U.S. PATENT DOCUMENTS

| | | | | |
|---|---|---|---|---|
| 6,154,031 | A * | 11/2000 | Hughes | G01R 33/3852 324/318 |
| 8,278,927 | B2 * | 10/2012 | Venkatesa | G01R 33/3852 324/309 |
| 9,075,102 | B2 * | 7/2015 | Ham | G01R 33/28 |
| 2013/0278267 | A1 | 10/2013 | Hori et al. | |
| 2014/0070809 | A1 | 3/2014 | Imamura et al. | |
| 2014/0070812 | A1 | 3/2014 | Yokoi et al. | |

FOREIGN PATENT DOCUMENTS

| | | |
|---|---|---|
| JP | 2001-516244 | 9/2001 |
| JP | 2012-016574 | 1/2012 |
| JP | 2013-236912 | 11/2013 |
| JP | 2014-064897 | 4/2014 |
| JP | 2014-064898 | 4/2014 |

* cited by examiner

MAGNETIC RESONANCE IMAGING DEVICE

CROSS-REFERENCE TO RELATED APPLICATIONS

This application is a continuation of PCT international application Ser. No. PCT/JP2013/068748 filed on Jul. 9, 2013 which designates the United States, incorporated herein by reference, and which claims the benefit of priority from Japanese Patent Application No. 2012-153831, filed on Jul. 9, 2012, the entire contents of which are incorporated herein by reference.

FIELD

Embodiments described herein relate generally to a magnetic resonance imaging device.

BACKGROUND

There is a pulse sequence for executing high-speed imaging, such as the echo planar imaging (EPI) sequence, as one of imaging methods by a magnetic resonance imaging device (MRI device). The MRI device includes a gradient amplifier for amplifying electric power that is supplied to a gradient coil. The gradient amplifier is requested to output high power for a short period of time in some cases, for example, at the time of application of the motion probing gradient (MPG) pulse in the EPI sequence. When the request is not satisfied, there arises a risk of an output voltage of the gradient amplifier being lowered while the pulse sequence is being executed and image quality is deteriorated.

DETAILED DESCRIPTION

A magnetic resonance imaging device according to an embodiment includes a gradient amplifier, a battery, a detector, and a battery controller. The gradient amplifier supplies electric power to the gradient coil. The battery is charged with electric power that is supplied from the power supply. The detector detects a high power output request on the gradient amplifier. The battery controller controls to supply electric power charged in the battery in addition to electric power supplied from the power supply to the gradient amplifier when the high power output request is detected.

Hereinafter, described is an MRI device according to embodiments with reference to the accompanying drawings.

First Embodiment

Figure 1:
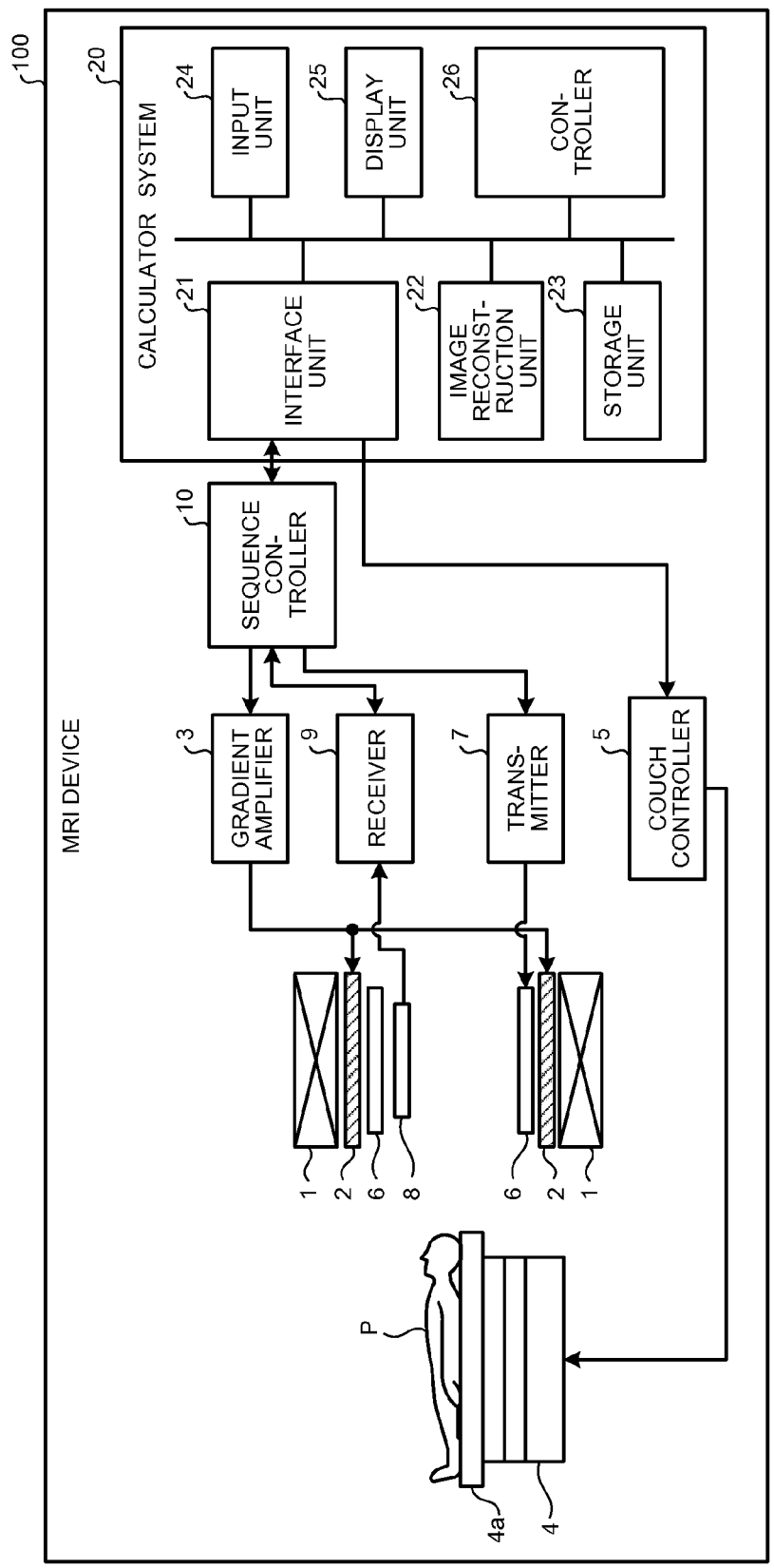
FIG. 1 is a diagram illustrating a configuration of an MRI device according to a first embodiment.

FIG. 1 is a diagram illustrating a configuration of an MRI device 100 according to a first embodiment. A subject P is not included in the MRI device 100. A magnetostatic magnet 1 is formed into a hollow cylindrical form and generates a uniform magnetostatic field in the inner space thereof. The magnetostatic magnet 1 is a permanent magnet, a superconducting magnet, or the like. A gradient coil 2 is formed into a hollow cylindrical form and generates a gradient magnetic field in the inner space thereof. To be more specific, the gradient coil 2 is arranged at the inner side of the magnetostatic magnet 1 and receives supply of electric power from a gradient amplifier 3 to generate a gradient magnetic field. The gradient amplifier 3 supplies electric power to the gradient coil 2 in accordance with a control signal that is transmitted from a sequence controller 10.

A couch 4 includes a couchtop 4a on which the subject P is placed. The couch 4 inserts the couchtop 4a into a bore of the gradient coil 2 serving as an imaging port in a state where the subject P is placed on the couchtop 4a. Normally, the couch 4 is installed such that the lengthwise direction thereof is parallel with the center axis of the magnetostatic magnet 1. A couch controller 5 drives the couch 4 so as to move the couchtop 4a in the lengthwise direction and the up-down direction.

A transmission coil 6 generates a radio-frequency magnetic field. To be more specific, the transmission coil 6 is arranged at the inner side of the gradient coil 2 and receives supply of a radio frequency pulse (hereinafter, "RF pulse") from a transmitter 7 so as to generate the radio-frequency magnetic field. The transmitter 7 transmits the RF pulse corresponding to a Larmor frequency to the transmission coil 6 in accordance with a control signal that is transmitted from the sequence controller 10.

A receiving coil 8 receives a magnetic resonance signal (hereinafter, "MR signal"). To be more specific, the receiving coil 8 is arranged at the inner side of the gradient coil 2 and receives the MR signal that is emitted from the subject P by influence of the radio-frequency magnetic field. Furthermore, the receiving coil 8 outputs the received MR signal to a receiver 9.

The receiver 9 generates MR signal data based on the MR signal output from the receiving coil 8 in accordance with a control signal that is transmitted from the sequence controller 10. To be more specific, the receiver 9 digital-converts the MR signal output from the receiving coil 8 so as to generate the MR signal data. Then, the receiver 9 transmits the generated MR signal data to a calculator system 20 through the sequence controller 10. It is noted that the receiver 9 may be included in a mount device including the magnetostatic magnet 1, the gradient coil 2, and the like.

The sequence controller 10 controls the gradient amplifier 3, the transmitter 7, and the receiver 9. To be more specific, the sequence controller 10 transmits a control signal based on pulse sequence execution data transmitted from the calculator system 20 to the gradient power supply 3, the transmitter 7, and the receiver 9.

The calculator system 20 includes an interface unit 21, an image reconstruction unit 22, a storage unit 23, an input unit 24, a display unit 25, and a controller 26. The interface unit 21 is connected to the sequence controller 10 and controls input/output of data that is transmitted and received between the sequence controller 10 and the calculator system 20. The image reconstruction unit 22 reconstructs image data based on the MR signal data transmitted from the sequence controller 10 and stores the reconstructed image data in the storage unit 23.

The storage unit 23 stores parameter values set for parameters contained in an imaging condition, image data stored by the image reconstruction unit 22, and other pieces of data that are used in the MRI device 100. For example, the storage unit 23 is a random access memory (RAM), a semiconductor memory device such as a flash memory, a hard disk, or an optical disk.

The input unit 24 receives various directions for editing the imaging condition, imaging directions, and the like from an operator. For example, the input unit 24 receives setting directions of the parameter values for the parameters contained in the imaging condition. For example, the input unit 24 is a mouse or a keyboard. The display unit 25 displays a screen for editing the imaging condition, images, and the like.

The controller 26 controls the above-mentioned parts so as to control the MRI device 100 comprehensively. For example, if the controller 26 receives edition of the imaging condition from the operator, the controller 26 generates pulse sequence execution data based on the received imaging condition and transmits the generated pulse sequence execution data to the sequence controller 10. For example, the controller 26 is an integrated circuit such as an application specific integrated circuit (ASIC) and a field programmable gate array (FPGA) or an electronic circuit such as a central processing unit (CPU) and a micro processing unit (MPU).

The MRI device 100 according to the first embodiment drives the above-mentioned gradient amplifier 3 using two types of power supplies including an equipment power supply and a battery. To be more specific, the MRI device 100 drives the gradient amplifier 3 using only electric power that is supplied from the equipment power supply in a normal state and adds electric power that is supplied from the battery if needed when a pulse sequence requesting high power is executed. The amount of the electric power that is supplied from the equipment power supply is monitored and controlled such that it does not exceed the suppliable amount of the equipment power supply.

Described is the difference between the "battery" and the "capacitor". The difference between the "battery" and the "capacitor" can be described based on a relation between an accumulated charge amount and an output voltage. On the "capacitor", the charge amount and the output voltage are proportional to each other. That is to say, the more electric charges are released, the lower the voltage value that can be output is. On the other hand, on the "battery", the charge amount and the output voltage are not proportional to each other. That is to say, even when the electric charges are released, a constant voltage can be output for a certain range of charge amount.

As described above, in the following embodiments, electric power that is supplied from the "battery" is used when the pulse sequence requesting high power is executed. In this point, the "capacitor" causes a risk of a pulse waveform changing while the pulse sequence is being executed because the charge amount and the output voltage are proportional to each other, whereas the "battery" makes it possible to keep the pulse waveform. It is noted that a secondary battery (for example, SCiB (registered trademark)) can be used as the battery.

Figure 2:
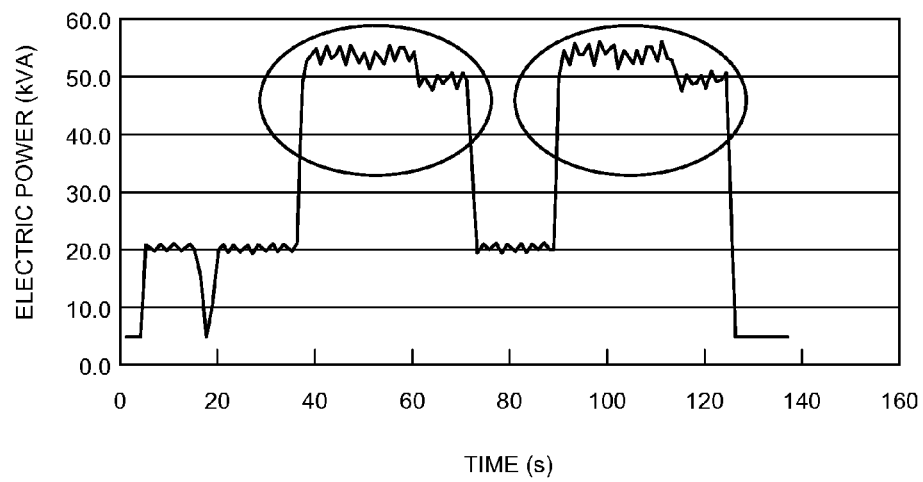
FIG. 2 is a graph for explaining a high power output request in the first embodiment.

FIG. 2 is a graph for explaining a high power output request in the first embodiment. FIG. 2 illustrates a part of temporal change of electric power requested on the gradient amplifier 3 when the EPI sequence is executed. High power output is requested on two portions surrounded by circles in FIG. 2. In the case of the EPI sequence, the two portions correspond to timings at which the motion probing gradient (MPG) pulse is applied, for example. Thus, the gradient amplifier 3 is requested to output high power for a short period of time (for example, ms order) in some cases. The EPI is one of high-speed imaging methods. A gradient magnetic field is inverted at high speed continuously for one nuclear magnetic excitation to generate echo continuously in the EPI. The MPG pulse is applied before the normal pulse sequence.

Figure 3:
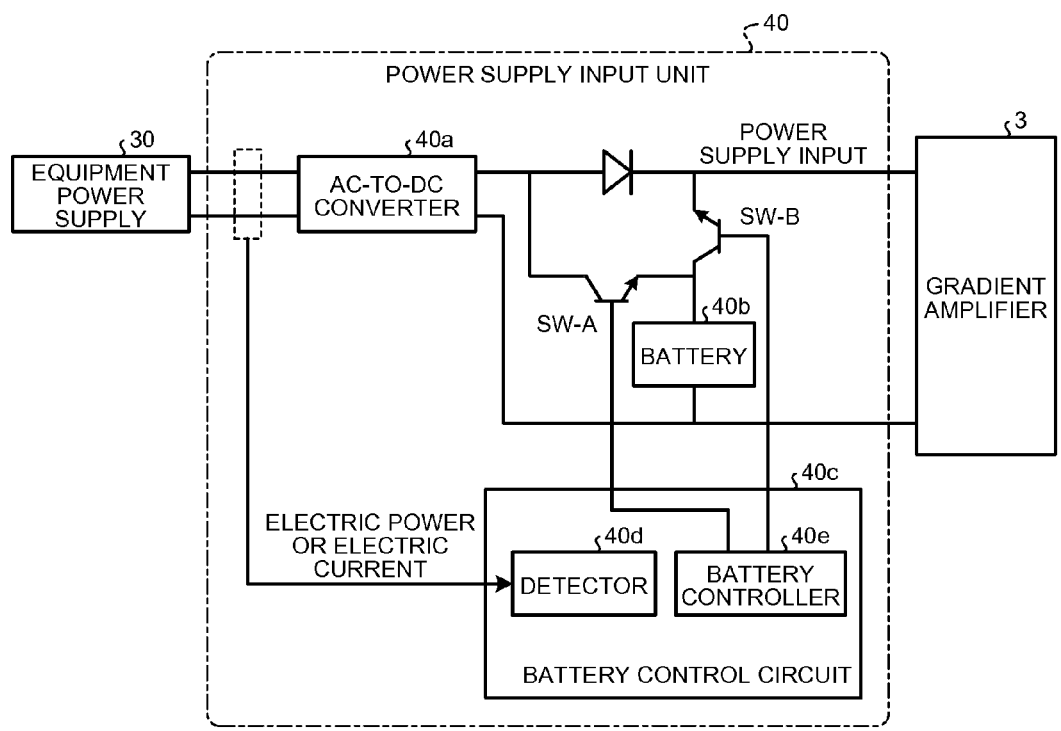
FIG. 3 is a diagram illustrating a configuration of a power supply input unit in the first embodiment.

FIG. 3 is a diagram illustrating a configuration of a power supply input unit 40 in the first embodiment. As illustrated in FIG. 3, both of an equipment power supply 30 and a battery 40b correspond to power supply sources of the gradient amplifier 3 in the first embodiment.

The gradient amplifier 3 includes the power supply input unit 40. The power supply input unit 40 controls input of electric power that is supplied from the equipment power supply 30. Although not illustrated in FIG. 1, the equipment power supply 30 is a power supply that supplies electric power to the MRI device 100 overall or the hospital in which the MRI device 100 is installed overall. Furthermore, the power supply input unit 40 may be arranged at the outer side of the housing of the gradient amplifier 3 or incorporated in the housing thereof.

The power supply input unit 40 includes an alternating current (AC)-to-direct current (DC) converter 40a, the battery 40b, and a battery control circuit 40c. The electric power of the equipment power supply 30 is supplied to the gradient amplifier 3 through the AC-to-DC converter 40a. The AC-to-DC converter 40a converts an electric current supplied from the equipment power supply 30 from an alternating current to a direct current.

The battery 40b is charged with electric power that is supplied from the equipment power supply 30 and supplies the charged power to the gradient amplifier 3. For example, when supplied power from the equipment power supply 30 is sufficient including the case where imaging is not performed and the case where a pulse sequence with small power consumption is being executed, the battery 40b is charged with the electric power that is supplied from the equipment power supply 30. Furthermore, the battery 40b discharges the charged power and supplies it to the gradient amplifier 3 under the condition that high power output is requested. The charge into the battery 40b and the discharge from the battery 40b are executed under control performed by the battery control circuit 40c.

Figure 4:
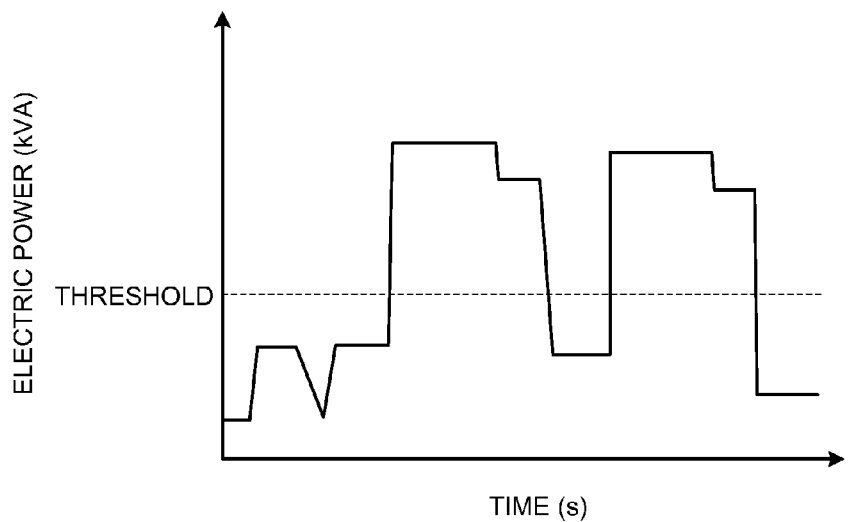
FIG. 4 is a graph for explaining a threshold in the first embodiment.

The battery control circuit 40c includes a detector 40d and a battery controller 40e. The detector 40d detects a high power output request on the gradient amplifier 3 based on an output power (or output current) value of the equipment power supply 30. In the first embodiment, the detector 40d previously sets, as a threshold, allowable power (or allowable current) of the equipment power supply 30 or a value (for example, a power value between a power value before application of the MPG pulse and a power value after the application of the MPG pulse) that is slightly smaller than the allowable power (or allowable current). FIG. 4 is a graph for explaining the threshold in the first embodiment. Shift of the power value illustrated in FIG. 4 corresponds to that illustrated in FIG. 2. The detector 40d monitors the output power (or output current) of the equipment power supply 30 continually (indicated by a dashed frame in FIG. 3) and determines whether the monitored output power (or output current) is equal to or lower than the threshold or reaches the threshold. Then, the detector 40d transmits the determination result to the battery controller 40e continually. Only when the monitored output power (or output current) reaches the threshold, the detector 40d may transmit a notification indicating the fact to the battery controller 40e, for example.

If the detector 40d detects the high power output request, the battery controller 40e controls to supply electric power charged in the battery 40b in addition to electric power supplied from the equipment power supply 30 to the gradient amplifier 3. For example, if the battery controller 40e receives the notification indicating that the output power (or output current) is equal to or lower than the threshold from the detector 40d, the battery controller 40e controls to turn an SW-A "ON" and turn an SW-B "OFF". Note that FIG. 3 illustrates the SW-A and the SW-B. When the SW-A and the SW-B are already controlled to the states, it is sufficient that the battery controller 40e does not control the SW-A and the SW-B. As a result, only the electric power from the equipment power supply 30 is supplied to the gradient amplifier 3 and the electric power from the equipment power supply 30 also charges the battery 40b in accordance with surplus power thereof.

On the other hand, if the battery controller 40e receives the notification indicating that the output power (or output current) reaches the threshold from the detector 40d, the battery controller 40e controls to turn the SW-A as illustrated in FIG. 3 "OFF" and turn the SW-B "ON". As a result, the electric power charged in the battery 40b is discharged. With this, the electric power charged in the battery 40b in addition to the electric power supplied from the equipment power supply 30 are supplied to the gradient amplifier 3. That is to say, the battery controller 40e assists power supply to the gradient amplifier 3 with the discharge of the electric power charged in the battery 40b so as to compensate insufficient power.

Figure 5:
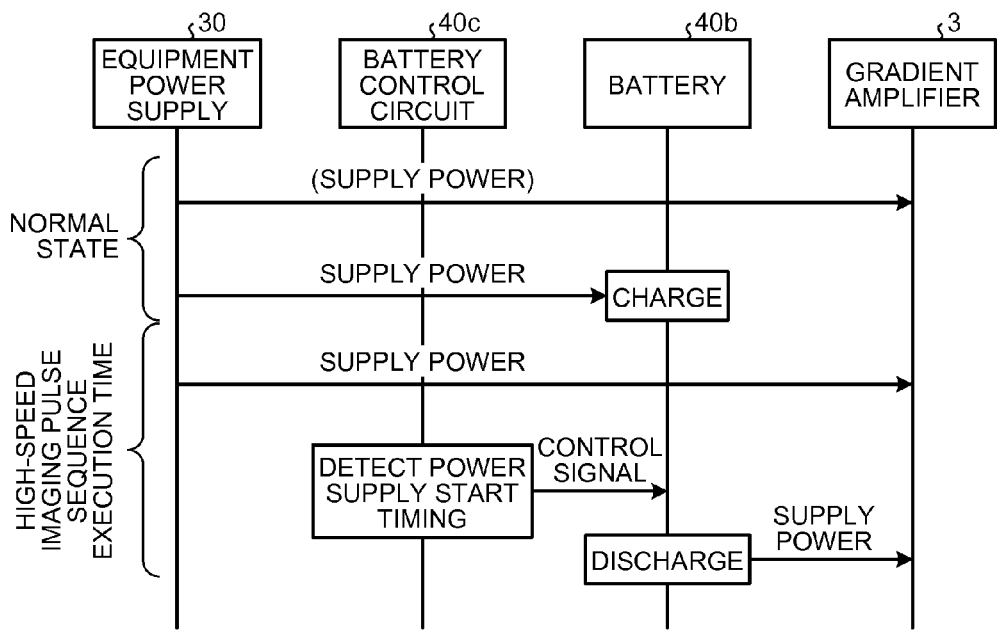
FIG. 5 is a diagram for explaining battery control in the first embodiment.

FIG. 5 is a diagram for explaining battery control in the first embodiment. As illustrated in FIG. 5, in the normal state where imaging is not performed, where a pulse sequence with small power consumption is being executed, or where the pulse sequence is being executed under the condition that high power output is not requested even in the case of the EPI sequence or the like, only the electric power from the equipment power supply 30 is supplied to the gradient amplifier 3 and the electric power from the equipment power supply 30 also charges the battery 40b in accordance with the surplus power thereof. Note that when imaging is not performed, the electric power from the equipment power supply 30 is not also supplied to the gradient amplifier 3 in principle.

On the other hand, in the high power output-requested state when the high-speed imaging pulse sequence is executed and high power output is just requested, the battery control circuit 40c detects a high power output request, that is, a power supply start timing by the battery 40b. As a result, the electric power from the equipment power supply 30 is supplied to the gradient amplifier 3 and the electric power charged in the battery 40b is discharged and supplied to the gradient amplifier 3.

For example, the battery controller 40e may switch "ON" and "OFF" of the SW-A and SW-B and stop discharge of the battery 40b at the timing when the output power (or output current) becomes lower than the threshold again (including the timing while the pulse sequence is being executed). In this case, for example, the battery 40b is discharged for only a period of time including before and after the application of the MPG pulse. Alternatively, the battery controller 40e may switch "ON" and "OFF" of the SW-A and SW-B and stop discharge of the battery 40b at the timing when one pulse sequence is executed completely, for example.

As described above, according to the first embodiment, the high power output request is detected by monitoring the output power (or output current) of the equipment power supply 30 so as to set both of the equipment power supply 30 and the battery 40b as power supply sources of the gradient amplifier 3. As a result, when the gradient amplifier 3 outputs high power, lowering of the output voltage can be suppressed. Eventually, image quality at the high-speed imaging can be ensured.

In addition, in the first embodiment, the battery is included in the power supply input unit 40 of the gradient amplifier 3. As a result, a large-sized equipment power supply in accordance with a high power output request needs not be prepared, thereby reducing the equipment power supply in size.

Second Embodiment

Figure 6:
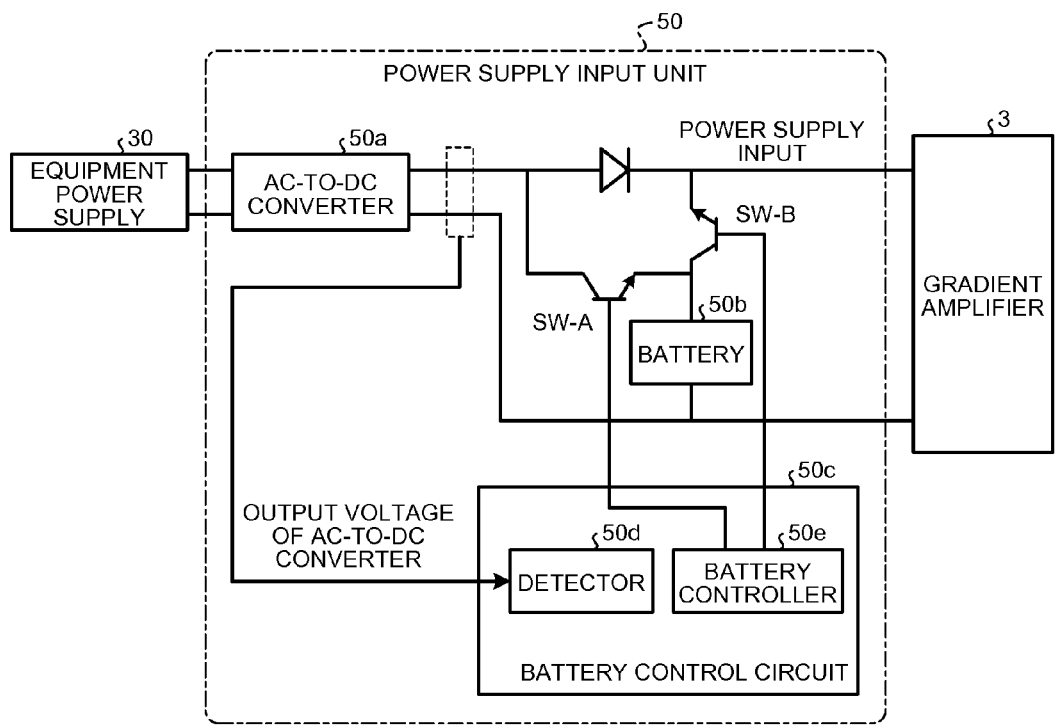
FIG. 6 is a diagram illustrating a configuration of a power supply input unit according to a second embodiment.

FIG. 6 is a diagram illustrating a configuration of a power supply input unit 50 in a second embodiment. The overall configuration of the MRI device 100 in the second embodiment is the same as that in the first embodiment.

In the second embodiment, an AC-to-DC converter 50a has a current restricting function. For example, when the gradient amplifier 3 requests high power output, the AC-to-DC converter 50a controls to lower a voltage so as not to output high power. On the other hand, a detector 50d detects the high power output request on the gradient amplifier 3 based on the output voltage of the AC-to-DC converter 50a. To be more specific, the detector 50d monitors the output voltage of the AC-to-DC converter 50a continually (indicated by a dashed frame in FIG. 6) and determines whether the monitored output voltage is equal to or higher than a threshold or reaches the threshold. Then, the detector 50d transmits the determination result to a battery controller 50e continually. Only when the monitored output voltage reaches the threshold, the detector 50d may transmit a notification indicating the fact to the battery controller 50e, for example.

Figure 7:
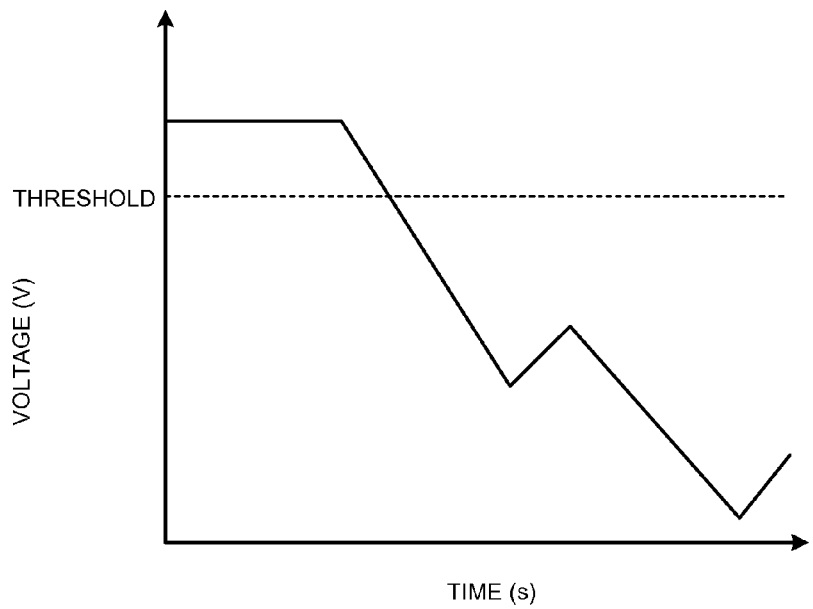
FIG. 7 is a graph for explaining a threshold in the second embodiment.

FIG. 7 is a graph for explaining the threshold in the second embodiment. Change of the voltage value as illustrated in FIG. 7 corresponds to the change of the power value as illustrated in FIG. 2 and FIG. 4. That is to say, in FIG. 7, the voltage drops twice and the timings of the voltage drop correspond to application of the MPG pulse twice. In the second embodiment, for example, it is sufficient that the detector 50d previously sets, as the threshold, a voltage value between a voltage value before application of the first MPG pulse and a voltage value after the application thereof.

In the same manner as in the first embodiment, if the detector 50d detects the high power output request, the battery controller 50e controls to supply electric power charged in a battery 50b in addition to electric power supplied from the equipment power supply 30 to the gradient amplifier 3. For example, if the battery controller 50e receives the notification indicating that the output voltage is equal to or higher than the threshold from the detector 50d, the battery controller 50e controls to turn an SW-A "ON" and turn an SW-B "OFF". Note that FIG. 6 illustrates the SW-A and the SW-B. When the SW-A and the SW-B are already controlled to the states, it is sufficient that the battery controller 50e does not control the SW-A and the SW-B. On the other hand, if the battery controller 50e receives the notification indicating that the output voltage reaches the threshold from the detector 50*d*, the battery controller 50*e* controls to turn the SW-A as illustrated in FIG. 6 "OFF" and turn the SW-B "ON".

As described above, according to the second embodiment, the high power output request is detected by monitoring the output voltage of the AC-to-DC converter 50*a* so as to set both of the equipment power supply 30 and the battery 50*b* as power supply sources of the gradient amplifier 3. As a result, as in the first embodiment, lowering of the output voltage can be suppressed, image quality at the high-speed imaging can be ensured, and the equipment power supply can be reduced in size.

Third Embodiment

Figure 8:
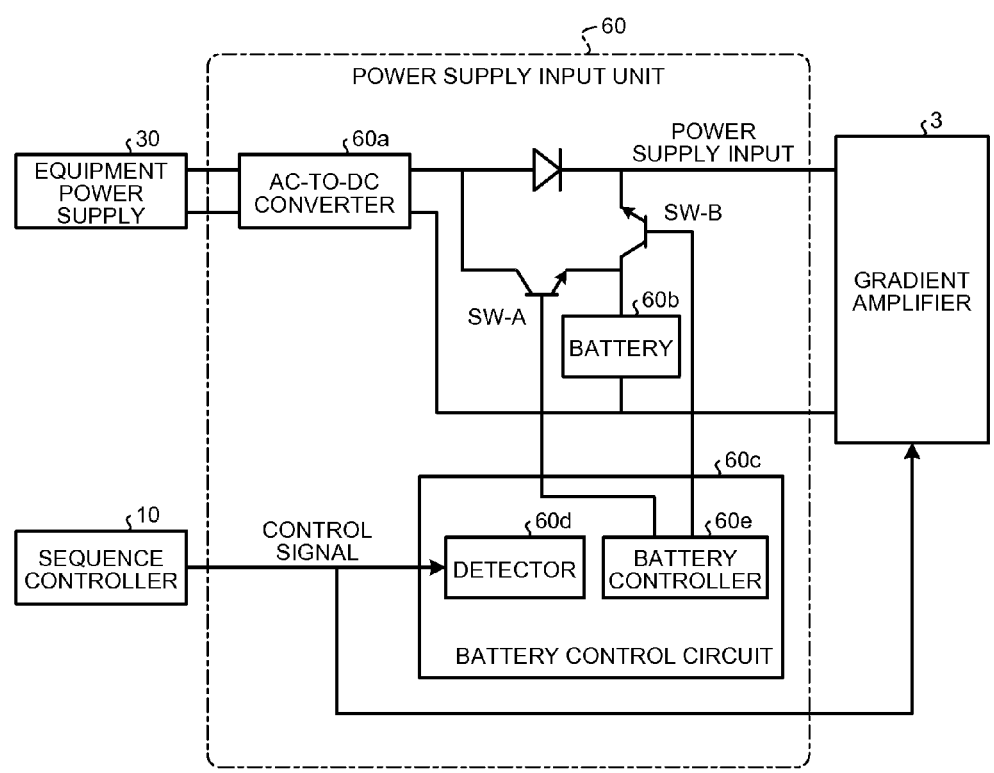
FIG. 8 is a diagram illustrating a configuration of a power supply input unit according to a third embodiment.

FIG. 8 is a diagram illustrating a configuration of a power supply input unit 60 in a third embodiment. The overall configuration of the MRI device 100 in the third embodiment is the same as that in the first embodiment.

In the third embodiment, a detector 60*d* detects a high power output request based on information of a pulse sequence defined by the imaging condition. A control signal that is transmitted to the detector 60*d* from the sequence controller 10 continually, for example, defines an intensity of an electric current to be supplied to the gradient coil 2 and a supply timing thereof. The detector 60*d* calculates electric power requested on the gradient amplifier 3 for every unit time based on the control signal and detects a high power output request when the calculated power is higher than the certain threshold. The detector 60*d* may estimate the usage amount of a battery 60*b* based on the calculated power and output a remaining amount of the battery 60*b* to the display unit 25 so as to notify an operator of the remaining amount.

In the same manner as in the first and the second embodiments, when the detector 60*d* detects the high power output request, a battery controller 60*e* controls to supply electric power charged in the battery 60*b* in addition to electric power supplied from the equipment power supply 30 to the gradient amplifier 3.

As described above, according to the third embodiment, the high power output request is detected based on the information of the pulse sequence defined by the imaging condition so as to set both of the equipment power supply 30 and the battery 60*b* as power supply sources of the gradient amplifier 3. As a result, as in the first and the second embodiments, lowering of the output voltage can be suppressed, image quality at the high-speed imaging can be ensured, and the equipment power supply can be reduced in size.

Other Embodiments

The embodiment is not limited to the above-mentioned embodiments. As a method of detecting the high power output request, for example, a plan of the high power output request may be detected at a stage of imaging design. The stage of the imaging design indicates a stage at which an operator inputs parameters of the imaging condition onto the screen for editing the imaging condition, for example. When a plurality of pulse sequences requesting high power output are specified on the imaging design, for example, the controller 26 of the calculator system 20 calculates electric power that is requested on the gradient amplifier 3. Then, when the controller 26 determines that the calculated power exceeds the allowable power obtained by summing electric power of the equipment power supply and electric power of the battery before the plurality of pulse sequences are executed completely, the controller 26 may control so as not to start imaging. The controller 26 may output the notification indicating the fact to the display unit 25 so as to notify the operator of it.

Furthermore, the controller 26 may, for example, control to change the execution order of the pulse sequences and optimize it in the above-mentioned case. In the imaging by the MRI device 100, for example, imaging of a positioning image, imaging of a sensitivity map, shimming imaging, and the like are also performed as preliminary imaging in addition to main imaging in some cases. The imaging of the sensitivity map is imaging for collecting data indicating a receiving sensitivity distribution of the receiving coil 8 when the receiving coil 8 is a multi-coil and the shimming imaging is imaging for collecting data for use in uniform correction of a magnetostatic intensity. It is considered to be sufficient that the imaging of the sensitivity map among these pieces of preliminary imaging is performed at least before reconstruction of an image. When the EPI sequence is performed repeatedly as the main imaging, the controller 26 may change the execution order of the pulse sequences such that the imaging of the sensitivity map is inserted between the EPI sequences. The controller 26 may output the change of the execution order thereof to the display unit 25 to notify the operator of it.

In general, it is considered that the charge into the battery is completed for approximately several seconds. In consideration of this point, it is sufficient that the controller 26 controls the timing of imaging restart and the execution order of the pulse sequences. Furthermore, the imaging control performed by the above-mentioned controller 26 is not limited to be performed by the controller 26 but may be performed in a battery control circuit.

Although the pulse sequence requesting high power output has been described by taking the EPI sequence as an example and the high power output is made for application of the MPG pulse in the above-mentioned embodiments, the embodiment is not limited thereto. Any pulse sequence is capable of detecting the high power output request by the same method as those in the above-mentioned embodiments so as to supply electric power from the battery as long as the pulse sequence requests the high power output.

The methods in the above-mentioned respective embodiments may be used in combination appropriately. Furthermore, although the battery is discharged at the very timing when the high power output is requested based on the real-time monitoring result and the like while the pulse sequence is being executed in the above-mentioned embodiments, the embodiment is not limited thereto. As described in other embodiments, for example, the controller 26 may specify a plan for executing the EPI sequence and control such that the battery is discharged from the start of the execution of the EPI sequence. The start timing of the discharge can be changed appropriately in accordance with the capacity of the battery and the like.

Combined Use of Capacitor

Although the driving method by two types of power supplies of the equipment power supply and the battery at the high power output-requested state has been described in the above-mentioned embodiments, the embodiment is not limited thereto and a capacitor may be used in combination with the battery.

Figure 9:
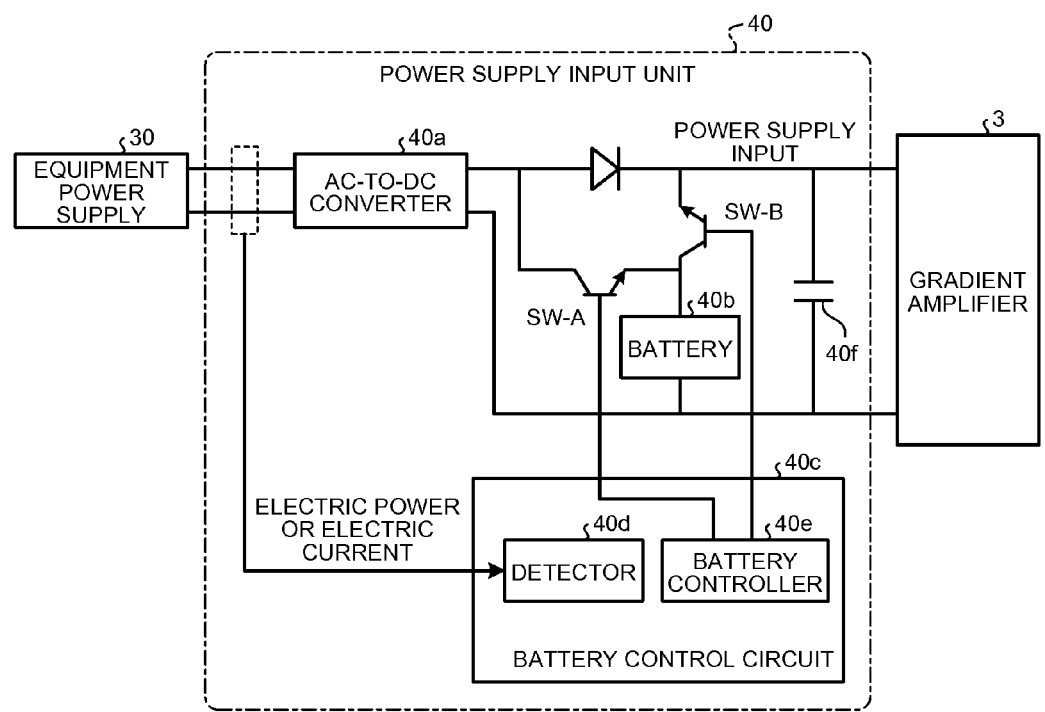
FIG. 9 is a diagram illustrating a configuration of a power supply input unit according to another embodiment.

FIG. 9 is a diagram illustrating a configuration of a power supply input unit in another embodiment. FIG. 9 illustrates an example in which a capacitor 40*f* is added to the power supply input unit 40 in the first embodiment. The capacitor 40f is charged with electric power that is supplied from the equipment power supply 30 or the battery 40b. Furthermore, the capacitor 40f supplies the electric power charged in the capacitor 40f to the gradient amplifier 3 in the high power output-requested state.

The "capacitor" has a characteristic that the larger the capacitor releases electric charges, the lower a voltage value that can be output is. Furthermore, the "capacitor" also has a characteristic that the reaction speed is high, that is, the time taken for charge and discharge is short. For example, when an inclination of the rising of a waveform is large as in the time of application of the MPG pulse in the EPI sequence, there is a risk of the reaction speed of the "battery" being incapable of responding to it. In this point, for example, as illustrated in FIG. 9, if the power supply input unit 40 includes the capacitor 40f in addition to the battery 40b, electric charges accumulated in the capacitor 40f are released if needed so as to cope with the pulse having a waveform with a large inclination. The "capacitor" can be, for example, used at the rising time and the "battery" can be used after the rising. Alternatively, the "capacitor" and the "battery" can be used in combination at the rising time and the "battery" can be used after the rising. Furthermore, the "capacitor" and the "battery" can be used in combination at the rising time and the "capacitor" and the "battery" can be also used in combination after the rising. The complementary relation between the "capacitor" and the "battery" can be changed arbitrarily.

In FIG. 9, although the capacitor 40f is added to the power supply input unit 40 in the first embodiment, the embodiment is not limited thereto. The capacitor can be also added to the power supply input unit 50 (see, FIG. 6) in the second embodiment and the power supply input unit 60 (see, FIG. 8) in the third embodiment and the battery and the capacitor can be used in combination as described above. Monitoring of Equipment Power Supply In the above-mentioned embodiments, the amount of electric power that is supplied from the equipment power supply is monitored and is controlled so as not to exceed the suppliable amount of the equipment power supply. The following describes this in greater detail. When the high power output request exceeds the suppliable amount of the equipment power supply, if no control is performed, there is a risk of power supply from a primary power supply being shut off by a breaker on the equipment power supply, for example.

In this point, in the first embodiment, the detector 40d monitors the output power (or output current) value of the equipment power supply continually. In the second embodiment, the detector 50d monitors the output voltage of the AC-to-DC converter continually. In the third embodiment, the detector 60d detects a high power output request based on the imaging condition. In this manner, in any cases of the above-mentioned embodiments, whether the output request to the equipment power supply exceeds the suppliable amount of the equipment power supply can be detected previously and electric power is supplied from the battery or the battery and the capacitor if needed. This can prevent, in the above-mentioned embodiments, shut-off of the power supply from the primary power supply on the equipment power supply.

The magnetic resonance imaging device according to at least one of the above-mentioned embodiments can suppress lowering of the output voltage of the gradient amplifier appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging device comprising:
a gradient amplifier configured to supply electric power to a gradient coil;
a battery configured to be charged with electric power that is supplied from a power supply;
a detector configured to detect a high power output request on the gradient amplifier; and
a battery controller configured to control to supply electric power charged in the battery in addition to electric power supplied from the power supply to the gradient amplifier when the high power output request is detected.

2. The magnetic resonance imaging device according to claim 1, wherein
the gradient amplifier includes a power supply input unit configured to control input of electric power that is supplied from the power supply, and
the battery is included in the power supply input unit.

3. The magnetic resonance imaging device according to claim 1, wherein the detector is configured to detect the high power output request based on an imaging condition.

4. The magnetic resonance imaging device according to claim 3, wherein the detector is configured to calculate electric power that is requested on the gradient amplifier for every unit time based on pulse sequence information defined by the imaging condition and detect the high power output request from the calculated electric power.

5. The magnetic resonance imaging device according to claim 1, further comprising an imaging controller configured to control so as not to start imaging when a plurality of pulse sequences requesting high power output are specified on an imaging design.

6. The magnetic resonance imaging device according to claim 1, further comprising an imaging controller configured to control to change an execution order of pulse sequences when a plurality of pulse sequences requesting high power output are specified on an imaging design.

7. The magnetic resonance imaging device according to claim 1, wherein the detector is configured to monitor output power or output current of the power supply and detect the high power output request when the output power or the output current reaches a certain threshold.

8. The magnetic resonance imaging device according to claim 1, wherein the detector is configured to monitor an output voltage of a converter arranged between the power supply and the gradient amplifier and detect the high power output request when the output voltage reaches a certain threshold.

9. The magnetic resonance imaging device according to claim 1, further comprising a capacitor configured to be charged with electric power that is supplied from the power supply or the battery, in addition to the battery, wherein
the battery controller is configured to control to supply electric power charged in the capacitor to the gradient amplifier when the high power output request is detected.

10. The magnetic resonance imaging device according to claim 9, wherein the electric power charged in the capacitor is supplied to the gradient amplifier at at least a rising time when a waveform of a pulse output from the gradient amplifier is a waveform with a large inclination.

\* \* \* \* \*